United States Patent [19]
Behre et al.

[11] Patent Number: 5,847,217
[45] Date of Patent: Dec. 8, 1998

[54] PROCESS FOR THE PREPARATION OF 2-AMINO-5-ALKYL-PHENOLS

[75] Inventors: Horst Behre; Guido Steffan, both of Odenthal, Germany

[73] Assignee: Bayer Aktiengesellschaft, Leverkusen, Germany

[21] Appl. No.: 982,360

[22] Filed: Dec. 2, 1997

[30] Foreign Application Priority Data

Dec. 9, 1996 [DE] Germany .................. 196 51 040.6

[51] Int. Cl.$^6$ .................................................. C07C 209/68
[52] U.S. Cl. ............................................. 564/394; 564/443
[58] Field of Search ...................................... 564/394, 443

Primary Examiner—Brian M. Burn
Attorney, Agent, or Firm—Sprung Kramer Schaefer & Briscoe

[57] ABSTRACT

2-Amino-5-alkyl-phenols, which are suitable as intermediates in the production of crop-protection agents or photographic couplers, can be prepared by subjecting 2-amino-5-alkyl-benzenesulphonic acids or their salts to alkaline hydrolysis.

11 Claims, No Drawings

PROCESS FOR THE PREPARATION OF 2-AMINO-5-ALKYL-PHENOLS

The present invention relates to a process for the preparation of 2-amino-5-alkyl-phenols, some of which are novel 2-amino-5-alkyl-phenols, and to their use as intermediates in the production of crop-protection agents and photographic chemicals.

2-Amino-5-alkyl-phenols are usually prepared by reducing the corresponding nitro compound, the 2-nitro-5-alkyl-phenol, for example by electrochemical reduction, as described in Stutts, J. Org. Chem. 54 (1989) 3740. A great disadvantage of this process is the availability of the 5-alkyl-2-nitro-phenols. According to DE-A-25 04 592, the preparation of 5-methyl-2-nitro-phenol, for example, involves a large number of steps.

We have found a process for the preparation of 2-amino-5-alkyl-phenols (I) which is characterized in that 2-amino-5-alkyl-benzenesulphonic acids or their salts are subjected to alkaline hydrolysis.

Preferred alkyl substituents of the compounds I which may be mentioned are $C_1$–$C_6$-alkyl, in particular $C_1$–$C_4$-alkyl radicals, particularly preferably methyl, ethyl, n-propyl, isopropyl, n-butyl, sec-butyl and tert-butyl. The process is particularly preferably suitable for the preparation of 2-amino-5-methyl-phenol, starting from 2-amino-5-methyl-benzenesulphonic acid.

The process according to the invention is preferably carried out at a temperature of from 250° to 400° C., particularly preferably at from 270° to 350° C., in particular at from 280° to 330° C. According to the process of the invention, the compounds I can, for example, be prepared by atmospheric fusion or under superatmospheric conditions, for example, by superatmospheric alkaline hydrolysis. If the reaction is carried out under superatmospheric conditions, suitable pressures are up to 120 bar, preferably from 2 to 120 bar, particularly preferably from 5 to 80 bar, in particular from 10 to 40 bar. These pressures can be the autogenous pressure of the reaction mixture, or be increased, in addition to the autogenous pressure, by injecting inert gas, for example nitrogen. The autogenous pressure of the reaction mixture is dependent on the mixing and concentration ratios in the reaction mixture and on the reaction temperature set, in a manner which in principle is familiar to the person skilled in the art. It is particularly dependent on the amount of water in the reaction mixture. If a pressure in the lower region of the said ranges is to be set, this can thus be achieved by releasing steam from the reaction mixture via a pressure relief valve.

The alkaline hydrolysis is preferably carried out in an aqueous alkali metal hydroxide. Examples of suitable aqueous alkali metal hydroxides for the process according to the invention are aqueous solutions of sodium hydroxide or potassium hydroxide, preferably mixtures of sodium hydroxide and potassium hydroxide, in particular potassium hydroxide. Solutions having a concentration of 50% by weight or more of alkali metal hydroxide, based on the total weight of the reaction mixture used for the alkaline hydrolysis, are particularly preferred. The concentration is particularly preferably from 50 to 96% by weight, very particularly preferably from 70 to 95% by weight, in particular from 75 to 90% by weight.

The quantity of alkali metal hydroxide used is preferably such that from 3 to 25 mol, preferably from 5 to 20 mol, in particular from 7 to 15 mol, of alkali metal hydroxide are present per mol of alkalimetal-2-amino-5-alkyl-benzenesulphonate in the reaction mixture used for the alkaline hydrolysis (i.e. before the hydrolysis). The said molar quantities of alkali metal hydroxide are based in this case on the sulphonate group, preferred examples of which are the sodium or potassium salts of 2-amino-5-alkyl-benzenesulphonic acid.

The 2-amino-5-alkyl-benzenesulphonic acids and their salts are preferably prepared by sulphonating the corresponding 4-alkyl-anilines using sulphuric acid. Sulphonation is preferably carried out in an inert organic solvent. The resulting sulphonic acids can then be neutralized in a known manner to give the corresponding sulphonates. If sulphonic acid salts are used, a corresponding neutralization during the process according to the invention is no longer required, meaning that an equivalent of alkali metal hydroxide required therefor is not required. However, neutralization to give the sulphonate can also be carried out in the process according to the invention by starting from 2-amino-5-alkyl-benzenesulphonic acids. Furthermore, it is also possible according to the invention to use the 2-amino-5-alkyl-benzenesulphonic acids or their alkali metal salts in dry or water-moist form or in the form of their aqueous solutions. Since it is preferable, in the process according to the invention, to base the molar amount of the aqueous alkali metal hydroxide on the sulphonate group, an additional amount of alkali metal hydroxide which is sufficient for the complete neutralization of all acid groups should be taken into account when free 2-amino-5-alkyl-benzenesulphonic acid or sulphonating mixtures containing this acid are used.

The reaction can, of course, also be carried out in the presence of inert organic solvents, for example decalin.

The 2-amino-5-alkyl-phenols can be isolated from the alkaline reaction mixture in various ways. Two variants A) and B) are mentioned by way of example.

Variant A)

The alkaline reaction mixture prepared by the process according to the invention is diluted with water and preferably adjusted to a pH of from 2.5 to 8.5, preferably from 3 to 7, in particular from 4 to 6, using a mineral acid in order to free the 2-amino-5-alkyl-phenol from the alkali metal salt initially formed during the alkali fusion. Examples of mineral acids which may be used are hydrochloric acid and/or sulphuric acid. In the process according to the invention the amount of water used to dilute the alkaline reaction mixture is preferably chosen such that the alkali metal salts formed during the above pH adjustment, for example sodium sulphate and/or sodium chloride and/or potassium sulfate and/or potassium chloride, are present in dissolved form during isolation of the 2-amino-5-alkyl-phenol prepared by the process according to the invention.

Variant B)

The alkaline reaction mixture prepared by the process according to the invention is diluted with water and preferably adjusted to a pH from 0 to 2.5 using a mineral acid at elevated temperature. The 2-amino-5-alkyl-phenol formed in the process according to the invention is converted into a water-soluble amine salt (hydrochloride and/or hydrogensulphate) and the alkali metal sulphite also formed decomposes, liberating sulphur dioxide. Examples of mineral acids which may be used are hydrochloric acid and/or sulphuric acid. In the process according to the invention the amount of water used to dilute the alkaline reaction mixture is preferably chosen such that the alkali metal salts formed during the acidification, for example sodium sulphate and/or sodium chloride and/or potassium sulphate and/or potassium chloride, are present in dissolved form. The 2-amino-5-alkyl-phenol is precipitated out by partial neutralization, with or without prior activated carbon clarification, to a pH of from 2.5 to 8.5, preferably from 3 to 7, in particular from 4 to 6, and isolated in the usual manner, for example by filtration and washing with water.

The 2-amino-5-alkyl-phenols which have been prepared by the process according to the invention are preferably isolated by the method in Variant B). The details of the preferred embodiment of the process according to the invention are as follows:

The Na salt of 2-amino-5-methyl-benzenesulphonic acid is reacted with 80% by weight of KOH to give the K salt of 2-amino-5-methyl-phenol (300° C.; 15 to 20 bar; 3h), the molar ratio of KOH to 2-amino-5-methyl-benzenesulphonic acid preferably being from 10:1 to 15:1. The reaction mixture is diluted to a content of approximately 5% by weight of 2-amino-5-methyl-phenol by direct expansion at 300° C. into water, or by pumping water into the autoclave after prior cooling to approximately 200° C. The resulting alkaline suspension of the K salt of 2-amino-5-methyl-phenol is metered into water at the same time as 36% by weight aqueous HCl at 90° C. at a pH of from 0.5 to 1.0. All the $SO_2$ is expelled from the resulting, aqueous, approximately 4% by weight 2-amino-5-methyl-phenol hydrochloride solution using nitrogen or by applying a vacuum, the solution is if necessary clarified using activated carbon to remove tarry constituents, and the 2-amino-5-methyl-phenol is precipitated out by neutralization of the hydrochloric acid solution, for example using aqueous sodium hydroxide at a pH of from 4.5 to 6.0, and isolated in the usual manner, for example by filtration and washing with water.

The process according to the invention can be carried out batchwise or continuously.

The invention further relates to the novel 2-amino-5-alkyl-phenols where alkyl represents $C_2$–$C_6$-alkyl, in particular $C_2$–$C_4$-alkyl.

The invention further relates to the use of compounds I as intermediates in the production of crop-protection agents and photographic materials. The use of compounds I as intermediates in the production of colour couplers is particularly preferred.

The compounds I prepared by the process according to the invention are particularly preferably used as intermediates in the production of crop-protection agents or, in particular, in the production of colour couplers.

In the production of colour couplers, the 2-amino-5-alkyl-phenol (I) is preferably reacted with an acid chloride to give an amide.

EXAMPLE I

A 1.3 l nickel autoclave was charged with 1050 g of 80% KOH (15.0 mol), followed by 187 g of 2-amino-5-methyl-benzenesulphonic acid (100% free acid) (M 187, 1.0 mol). After flushing with nitrogen, the reaction mixture (suspension) was heated to 300° C. over the course of approximately 2 h, the stirrer only being switched on from 180° C., and further stirred for approximately 5 h at 300° C. and a pressure of from 15 to 20 bar. After the autoclave had been cooled to 100° C., it was completely emptied and the reaction mixture was discharged into 1000 g of water. The resulting alkaline solution of the Na salt of 2-amino-5-methyl-phenol having a content of approximately 3.5% by weight of 2-amino-5-methyl-phenol (M 123; by HPLC) was metered into 200 g of water at the same time as 1700 g of 37% HCl (17.2 mol) at 100° C. and a pH of from 0.5 to 1.0 over the course of approximately 1 h. After all the $SO_2$ had been removed using nitrogen, the resulting hydrochloric acid solution of 2-amino-5-methyl-phenol hydrochloride containing approximately 1.7% by weight of 2-amino-5-methyl-phenol (M 123; by HPLC) was clarified using 20 g of active carbon at 100° C. to remove tarry constituents. The 2-amino-5-methyl-phenol was then removed from the clarified solution under a protective gas (nitrogen) by adding 50% NaOH at 60° C. until the pH was from 4.5 to 5.0 and the resulting aqueous 2-amino-5-methyl-phenol suspension was cooled to 20° C. at 10 K/h with stirring.

The product, which can be readily filtered, was isolated using a glass suction filter, washed with a total of 70 g of cold water in two equal portions and dried in vacuo (100 mbar) at 40° C.

74 g of 2-amino-5-methyl-phenol were obtained.

The composition of the isolated product was determined by HPLC and is as follows:

99.8% by weight of 2-amino-5-methyl-phenol
0.1% by weight of 4-methyl-pyrocatechol
0.1% by weight of unknown compounds The yield of 2-amino-5-methyl-phenol is 60% of theory, based on 2-amino-5-methyl-benzenesulphonic acid used.

What is claimed is:

1. A process for the preparation of 2-amino-5-alkyl-phenols, wherein 2-amino-5-alkyl-benzenesulphonic acids or their salts are subjected to alkaline hydrolysis.

2. The process according to claim 1, wherein alkyl represents $C_1$–$C_4$-alkyl.

3. The process according to claim 1, wherein alkyl represents methyl.

4. The process according to claim 1, wherein the alkaline hydrolysis is carried out at a temperature of from 250° to 400° C.

5. The process according to claim 1, wherein the alkaline hydrolysis is carried out at a temperature of from 270° to 350° C.

6. The process according to claim 1, wherein the alkaline hydrolysis is carried out at a temperature of from 280° to 300° C.

7. The process according to claim 1, wherein the alkaline hydrolysis is carried out in an aqueous alkali metal hydroxide having an alkali metal concentration of 50 or more % by weight, based on the total weight of the reaction mixture used for the alkaline hydrolysis.

8. The process according to claim 1, wherein the alkaline hydrolysis is carried out in an aqueous alkali metal hydroxide having an alkali metal concentration of from 50 to 96% by weight, based on the total weight of the reaction mixture used for the alkaline hydrolysis.

9. The process according to claim 1, wherein the alkaline hydrolysis is carried out in an aqueous alkali metal hydroxide, the quantity of alkali metal hydroxide being such that from 3 to 25 mol of alkali metal hydroxide, are present per mol of alkali metal 2-amino-5-methyl-benzenesulphonate in the reaction mixture used for the alkaline hydrolysis.

10. The process according to claim 1, wherein the alkaline hydrolysis is carried out in an aqueous alkali metal hydroxide, the quantity of alkali metal hydroxide being such that from 5 to 20 mol of alkali metal hydroxide, are present per mol of alkali metal 2-amino-5-methyl-benzenesulphonate in the reaction mixture used for the alkaline hydrolysis.

11. The process according to claim 1, wherein the 2-amino-5-alkyl-benzenesulphonic acids or their salts have been obtained by sulphonation of the corresponding 4-alkylanilines using sulphuric acid, with or without subsequent neutralization.

* * * * *